(12) United States Patent
Hansson

(10) Patent No.: US 10,463,262 B2
(45) Date of Patent: Nov. 5, 2019

(54) INSTRUMENT FOR USE IN MEASURING BLOOD FLOW IN THE FEMORAL HEAD

(71) Applicant: SWEMAC INNOVATION AB, Linköping (SE)

(72) Inventor: Henrik Hansson, Vreta Kloster (SE)

(73) Assignee: SWEMAC INNOVATION AB, Linkoping (SE)

( * ) Notice: Subject to any disclaimer, the term of this patent is extended or adjusted under 35 U.S.C. 154(b) by 324 days.

(21) Appl. No.: 15/107,939

(22) PCT Filed: Dec. 30, 2013

(86) PCT No.: PCT/SE2013/051627
§ 371 (c)(1),
(2) Date: Jun. 24, 2016

(87) PCT Pub. No.: WO2015/102522
PCT Pub. Date: Jul. 9, 2015

(65) Prior Publication Data
US 2016/0317045 A1 Nov. 3, 2016

(51) Int. Cl.
*A61B 5/02* (2006.01)
*A61B 5/026* (2006.01)
(Continued)

(52) U.S. Cl.
CPC ........ *A61B 5/026* (2013.01); *A61B 5/150015* (2013.01); *A61B 5/150633* (2013.01);
(Continued)

(58) Field of Classification Search
CPC ....... A61B 1/317; A61B 5/026; A61B 5/4504; A61B 5/4571; A61B 2010/008;
(Continued)

(56) References Cited

U.S. PATENT DOCUMENTS

2007/0185380 A1* 8/2007 Kucklick ........... A61B 1/00135
600/114
2008/0312545 A1* 12/2008 Nyarady ................ A61B 1/317
600/504
(Continued)

FOREIGN PATENT DOCUMENTS

WO 2007097702 8/2007
WO 2007126888 11/2007
(Continued)

OTHER PUBLICATIONS

Article entitle Early Prediction of Femoral Head Avascular Necrosis Following Neck Fracture, (2011, pp. 79-88).

*Primary Examiner* — Navin Natnithithadha
*Assistant Examiner* — Andrey Shostak
(74) *Attorney, Agent, or Firm* — Tarolli, Sundheim, Covell & Tummino LLP

(57) ABSTRACT

An instrument (1) for use in measuring blood flow in the femoral head after a femoral neck fracture comprises a sleeve (2) and a rod (3) which is displaceably mounted in the sleeve. The sleeve (2) is configured for insertion into a bore (4) in the femoral neck (5) and femoral head (6) and provided with at least one aperture (8) at a front portion (2a) thereof. The aperture (8) in the front portion (2a) of the sleeve (2) is intended for location in the femoral head (6) distally of the fracture (7) after the sleeve has been inserted into said bore (4). The rod (3) is configured for closing the aperture (8) in the sleeve (2) during insertion of the sleeve into the bore (4) in the femoral neck (5) and femoral head (6) and for exposing said aperture after said insertion. Thereby, blood leaking into the bore (4) at the front portion (2a) of the sleeve (2) can be collected by the sleeve through the aperture (8) therein for subsequent measuring of the volume of the collected blood.

3 Claims, 4 Drawing Sheets

(51) Int. Cl.
    *A61B 10/00*     (2006.01)
    *A61B 5/15*     (2006.01)
    *A61B 17/17*     (2006.01)
    *A61B 5/00*     (2006.01)

(52) U.S. Cl.
    CPC ...... *A61B 10/0045* (2013.01); *A61B 17/1739* (2013.01); *A61B 5/4538* (2013.01); *A61B 5/4571* (2013.01); *A61B 2010/008* (2013.01)

(58) Field of Classification Search
    CPC ........ A61B 5/150015; A61B 5/150633; A61B 5/4538; A61B 10/0045
    See application file for complete search history.

(56) References Cited

U.S. PATENT DOCUMENTS

| | | | |
|---|---|---|---|
| 2013/0144144 A1 | 6/2013 | Laster et al. | |
| 2014/0031794 A1* | 1/2014 | Windolf ............ | A61B 17/8811 604/513 |

FOREIGN PATENT DOCUMENTS

| | | |
|---|---|---|
| WO | 2008135798 | 11/2008 |
| WO | 2012142716 | 10/2012 |

* cited by examiner

INSTRUMENT FOR USE IN MEASURING BLOOD FLOW IN THE FEMORAL HEAD

RELATED APPLICATION

This application corresponds to PCT/SE2013/051627, files Dec. 30, 2013, the subject matter, of which is incorporated herein by reference in its entirety.

TECHNICAL FIELD

The present invention relates to an instrument for use in measuring the blood flow in the femoral head after a femoral neck fracture.

BACKGROUND OF THE INVENTION

The circulation of blood in the femoral head is often destroyed at a dislocated fracture. If there is inadequate circulation of blood, a necrosis of the femoral head will develop and prosthesis implantation is the most likely course of treatment. Inadequate blood flow in the neck of the femur may lead to inadequate healing of the femoral head after a fracture and may cause osteonecrosis, a disease that results from loss of blood supply to the bone where the bone tissue dies and may eventually collapse. If a bone involved in osteonecrosis is near a joint, e.g. the femoral head, it often leads to the collapse of the joint surface. On the other hand, if there is adequate circulation of blood in the femoral head, the femoral head remains alive and in this way the fracture is capable of healing. Here, the most likely surgical solution is to perform osteosynthesis. Thus, the determination of whether there is adequate circulation is an important step in the overall treatment regimen.

A reliable method for measuring blood flow in the bone before and during surgery will impact treatment selection, which will likely result in an improvement of the clinical outcome, minimization of cost and prevention of long term disability. Furthermore, accurate measurement of blood flow is important for orthopaedic research due to close correlation of the flow with bone formation and mineral deposition. Accurate measurements may also allow secondary predictions of bone activity in other bone disorders.

Instruments for measuring the blood flow in bones such as the femoral head after a femoral neck fracture are already known from e.g. WO 2007/126888 and WO 2008/135798.

These prior art blood measuring instruments however, have a rather complex construction and are circumstantial to use.

Thus, there is presently a great need for an instrument that can give an accurate and more immediate determination of circulation flow and that is of a simple construction and easy to use.

SUMMARY OF THE INVENTION

In accordance with the present invention, an instrument is suggested for use in measuring blood flow in the femoral head after a femoral neck fracture. The instrument comprises a sleeve and a rod which is displaceably mounted in the sleeve. The sleeve is configured for insertion into a bore drilled in the femoral neck and femoral head and is provided with at least one aperture at a front portion thereof. The aperture in the front portion of the sleeve is intended for location in the femoral head distally of the fracture after the sleeve has been inserted into said bore. The rod is configured for closing the at least one aperture in the sleeve during insertion of the sleeve into the bore in the femoral neck and femoral head and for exposing said at least one aperture after said insertion. Thereby, blood leaking into the bore at the front portion of the sleeve, e.g. in front of the front portion, can be collected by the sleeve through the at least one aperture therein for subsequent measuring of the volume of the collected blood.

According to the invention, the at least one aperture in the front portion of the sleeve can be provided in the front surface thereof or in a lateral surface of said front portion.

According to the invention, the rod comprises a front portion which is capable of closing the at least one aperture in the front portion of the sleeve by engaging said aperture and exposing said at least one aperture by either withdrawal therefrom, i.e. displacement of the rod in a direction away from the front portion of the sleeve, or, if the rod is configured with a front portion which is provided with a lateral aperture, by rotation of the rod until the lateral apertures in the sleeve as well as in the front portion of the rod are aligned.

According to the invention, the blood flowing into the sleeve through the at least one aperture in the front portion thereof, can be collected in a reservoir in the sleeve or discharged from the sleeve for collection after withdrawal of the rod from the aperture in the sleeve or after complete withdrawal of the rod from the sleeve. The volume of the collected blood is measured after a predetermined time period and this volume should then preferably lie above a certain value if the blood flow in the femoral head should be regarded as satisfying.

BRIEF DESCRIPTION OF THE DRAWINGS

The invention will be further described below with reference to the accompanying drawings, in which.

DETAILED DESCRIPTION OF PREFERRED EMBODIMENTS

As already mentioned, the present invention relates to an instrument for use in measuring the blood flow in the femoral head after a femoral neck fracture.

The instrument 1 comprises a sleeve 2 and a rod 3 which is displaceably mounted in the sleeve.

Figure 1:
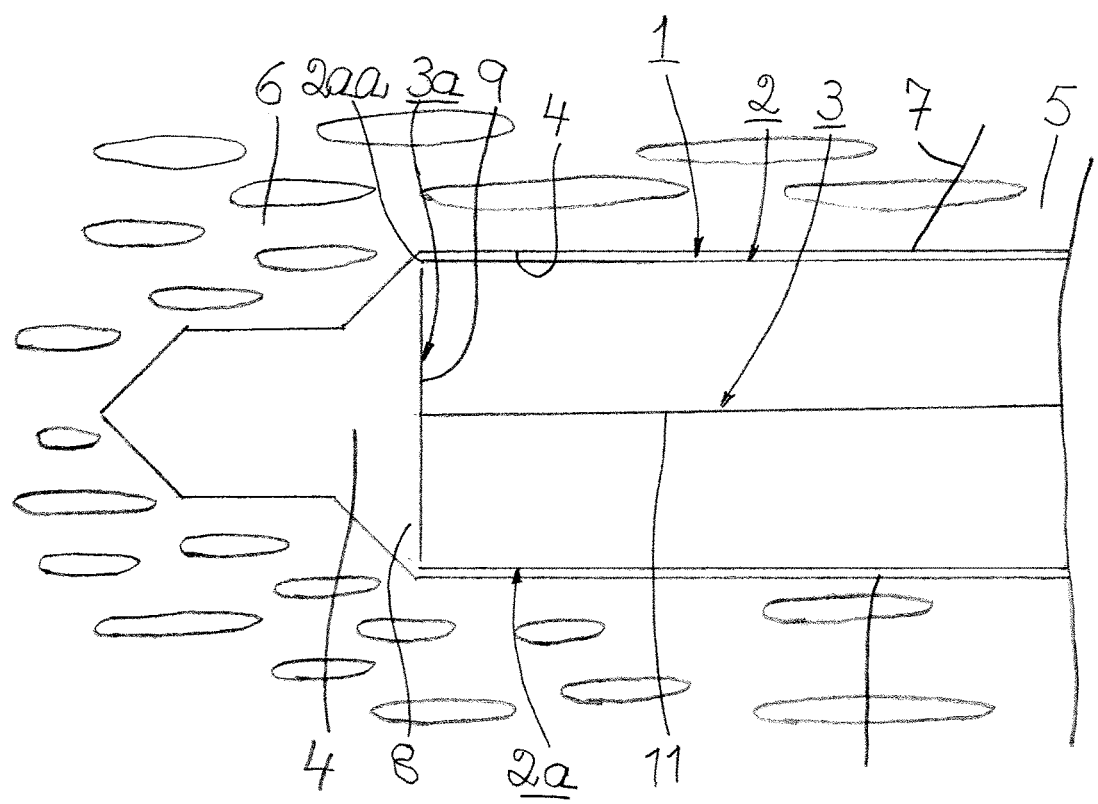
FIG. 1 is a very schematic sectional view of a first embodiment of the instrument according to the invention during insertion thereof into a bore in the femoral neck and femoral head.
Figure 2:
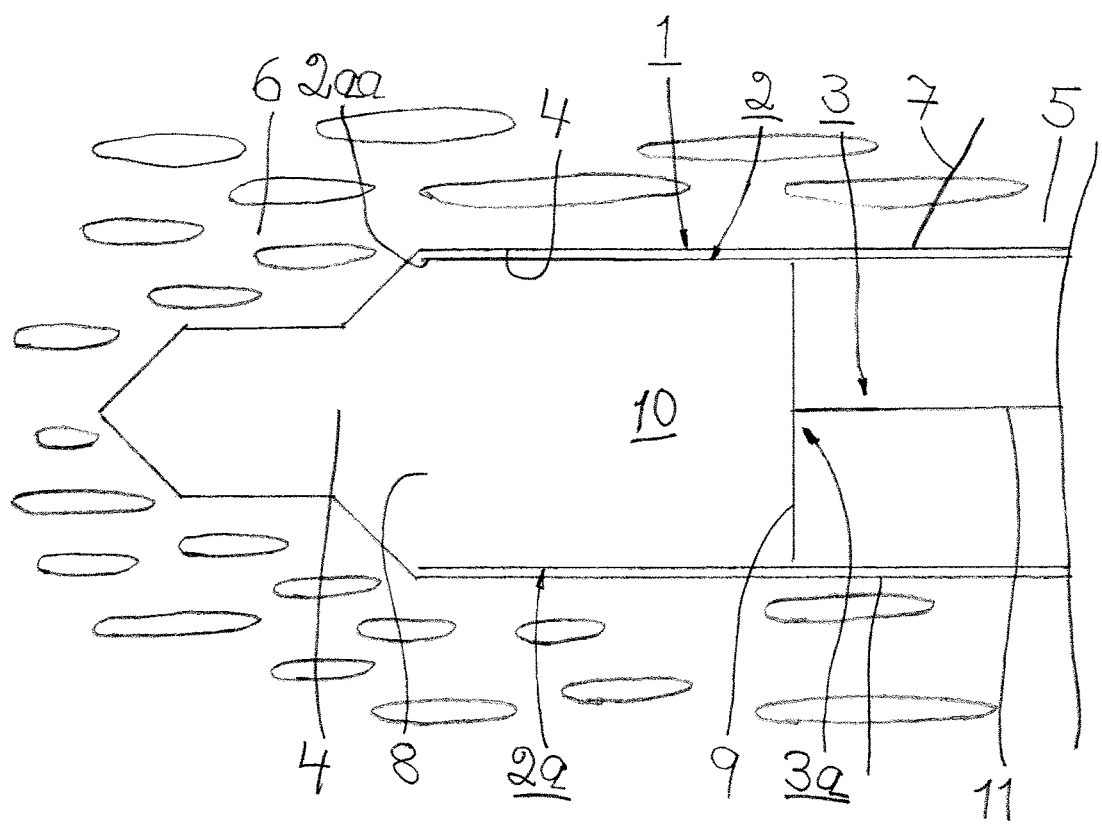
FIG. 2 is a very schematic sectional view of the first embodiment of the instrument according to the invention after insertion thereof into a bore in the femoral neck and femoral head and ready for collection of blood.
Figure 3:
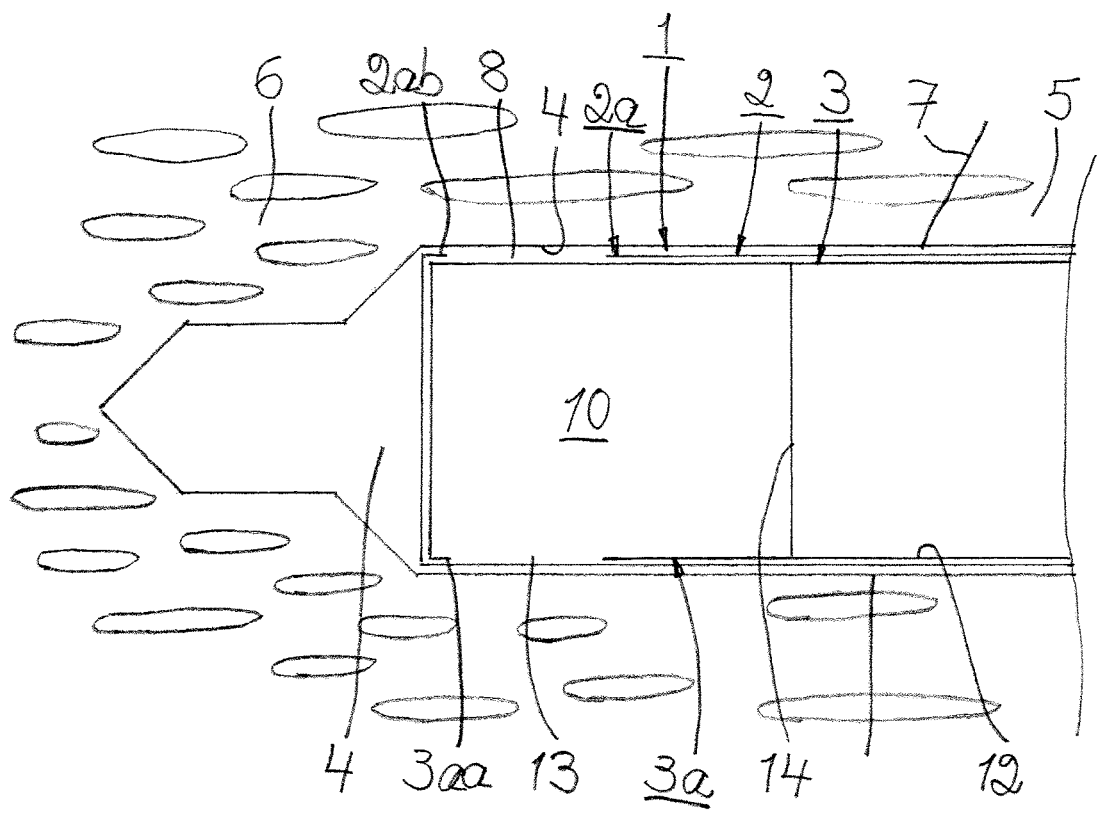
FIG. 3 is a very schematic sectional view of a second embodiment of the instrument according to the invention during insertion thereof into a bore in the femoral neck and femoral head.
Figure 4:
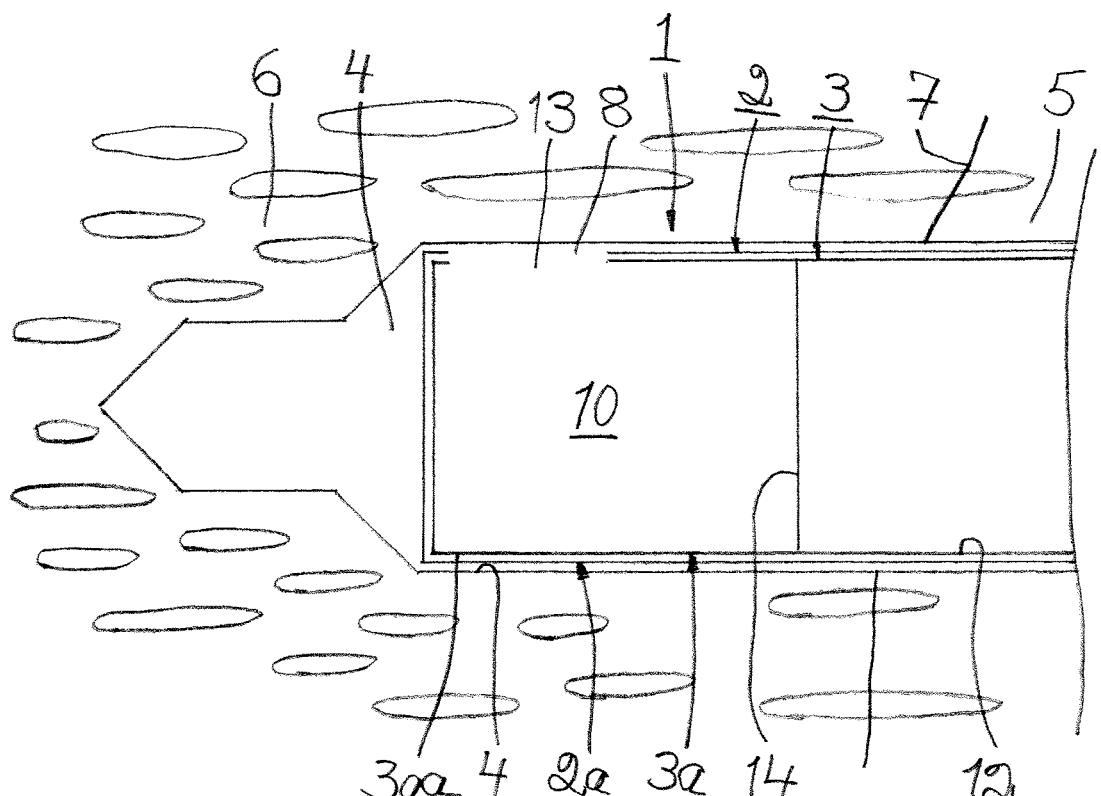
FIG. 4 is a very schematic sectional view of the second embodiment of the instrument according to the invention after insertion thereof into a bore in the femoral neck and femoral head and ready for collection of blood.

The sleeve 2 is configured for insertion into a bore 4 drilled in the femoral neck 5 and femoral head 6 past the fracture 7 and provided with at least one aperture 8 at a front portion 2a thereof. The sleeve 2 is inserted into said bore 4 until e.g. at least 10 mm and preferably about 20 mm of the bore is still free in front of the front portion 2a of said sleeve. The aperture 8 may be provided in a front surface 2aa of the front portion 2a of the sleeve 2, as is illustrated in FIGS. 1 and 2, and thereby cover the entire front surface or only a part thereof. The aperture 8 may alternatively be provided in a lateral surface 2ab of the front portion 2a of the sleeve 2, as is illustrated in FIGS. 3 and 4. Instead of one aperture 8, there may of course be two or more apertures in the respective surface 2aa, 2ab and the size of the aperture/apertures may vary. The aperture 8 in the front portion 2a of the sleeve 2 as illustrated, is in any case intended for location in the femoral head 6 distally of the fracture 7 after the sleeve has been inserted into said bore 4, while otherwise blood from a hematoma at the fracture may flow into the sleeve through the aperture 8 and give an incorrect measurement result. Thus, the bore 4 should have a length such that the aperture 8 is located in the femoral head 6 distally of the fracture 7 after the sleeve has been inserted into said bore and such that e.g. at least 10 mm, preferably about 20 mm of the bore still is free in front of the front portion 2a of said sleeve.

The rod 3 is configured for closing the at least one aperture 8 in the sleeve 2 during insertion of the sleeve into the bore 4 in the femoral neck 5 and femoral head 6 (see FIGS. 1 and 3) and for exposing said at least one aperture after said insertion (see FIGS. 2 and 4). Thereby, blood leaking into the bore 4 at the front portion 2a of the sleeve 2, e.g. into the at least 10 mm and preferably about 20 mm of the bore in front of the front portion, can be collected by the sleeve through the at least one aperture 8 therein for subsequent measuring of the volume of the collected blood after a predetermined time period, e.g. after about 5 minutes.

Accordingly, the rod 3 comprises a front portion 3a which is configured for closing said at least one aperture 8 in the front portion 2a of the sleeve 2 by bringing said front portion into engagement with the aperture or with the interior of the sleeve around said aperture and for exposure thereof by withdrawal of said front portion from said aperture.

For closing the aperture 8 in the front surface 2aa of the front portion 2a of the sleeve 2, the front portion 3a of the rod 3 may, as illustrated in FIGS. 1 and 2, be configured as a plate 9 having substantially the same cross-sectional area and size (diameter) as the interior of the sleeve or at least a size such that it covers the aperture in said front surface. In the former case, a reservoir 10 for collecting blood can be formed in the sleeve 2 in front of the front portion 3a of the rod 3 or the rod is withdrawn completely from the sleeve and the blood collected outside the sleeve. In the latter case, if the aperture 8 covers only a part of the front surface 2aa, the rod 3 need not be completely withdrawn from the sleeve 2. The blood will then instead flow around the plate 9 and out of the sleeve 2 for collection outside said sleeve. As illustrated in FIGS. 1 and 2, the plate 9 of the rod 2 is connected to a shaft 11 for operating the plate. Alternatively, the rod 3 may have the same cross-sectional area and size (diameter) along its entire length as long as it is the same as the interior of the sleeve or at least such that it covers the aperture in said front surface.

According to another alternative illustrated in FIGS. 3 and 4 for closing the aperture 8 in the lateral surface 2ab of the front portion 2a of the sleeve 2, the front portion 3a of the rod 3 may be configured more like a cylinder 12 having the same cross-sectional area and size (diameter) as the interior of the sleeve and a length such that it covers said aperture. Thus, the front portion 3a, in the form of a cylinder 12, of the rod 3 is configured for closing said at least one aperture 8 in the lateral surface 2ab in the front portion 2a of the sleeve 2 by bringing said front portion into engagement with the aperture. As illustrated in FIGS. 3 and 4, the front portion 3a of the rod 3 may be rotatable and provided with at least one aperture 13 in a lateral surface 3aa thereof for exposure of the lateral aperture 8 in the sleeve 2 by rotation of the rod such that the lateral aperture in the front portion thereof is aligned with the lateral aperture in the sleeve. The cylinder may be configured with a bottom surface 14 located below the aperture 8 in the lateral surface 2ab of the front portion 2a of the sleeve 2, thereby forming a reservoir 10 for collecting blood. The cylinder may also be withdrawn completely from the sleeve and the blood collected outside the sleeve. The cylinder form may continue beneath the bottom surface 14, i.e. may have the same cross-sectional area and size (diameter) along its entire length, or the cylinder may at said bottom surface be connected to a shaft for operating the cylinder as in the first embodiment of the instrument 1. Instead of being configured as a cylinder, the rotatable front portion 3a of the rod 3 may have the form of an arcuate wall member of a sufficient extension for being capable of covering the aperture 8 in the lateral surface 2ab of the front portion 2a of the sleeve 2.

Before the instrument according to the invention is used, the femoral neck fracture must be reposed. Then, guide wires may be inserted into the femoral neck 5 and femoral head 6 in order to fix the bone fragments of the femoral neck fracture 7. A bore is drilled into the femoral neck 5 and femoral head 6. A guide wire may be used as a guide for drilling. A thread may be cut into the bore and a screw driven into the bore for fixation of the fracture 7 or the bore 4 is used for insertion of the sleeve 2 and the rod 3 inside said sleeve into said bore. Otherwise, in the former case, a second bore 4 is drilled into the femoral neck 5 and femoral head 6 for insertion of the sleeve 2 with rod 3. The bore 4 in the femoral neck 5 and femoral head 6 for the sleeve 2 has of course a diameter which is somewhat larger than the external diameter of the sleeve. The sleeve 2 with the rod 3 inside said sleeve is now inserted into the bore 4 in question until the front portion 2a of the sleeve, provided with one or more apertures 8, has passed the fracture 7 and the possible hematoma at the fracture. During the insertion, the front portion 3a of the rod 3 engages the at least one aperture 8 in the front portion 2a of the sleeve 2 such that said aperture is closed and blood in the bore can not flow into the sleeve through the aperture. After insertion, the aperture 8 in the front portion 2a of the sleeve 2 is exposed either by withdrawal of the front portion 3a of the rod 3 from the aperture or rotation of said front portion relative to the front portion of the sleeve. Blood can now flow into the sleeve 2 through the aperture 8 therein. If the rod 3 is withdrawn completely from the sleeve 2, the blood is collected outside said sleeve for measuring the collected volume thereof after a predetermined time period, e.g. after about 5 minutes. Alternatively, as indicated above, the front portion 3a of the rod 3 may be withdrawn only to form a reservoir 10 in the sleeve 2 for collecting the blood therein or the rod may be configured such that a reservoir is formed in the sleeve or in the front portion of the rod. After a predetermined time period, e.g. about 5 minutes, the instrument is removed from the bore 4 and the blood collected in the reservoir 10 is measured.

Depending on the volume of the collected blood, it is now decided whether a prosthesis need to be implanted or measures should be taken to heal the fracture. A rough estimation of the volume can be performed, i.e. if no blood is collected, a prosthesis must be implanted, if a relatively small volume is collected, a decision must be taken whether the collected volume is sufficient for taking measures to heal the fracture or not and if a relatively large volume of blood is collected, measures should be taken to heal the fracture. Then, in time, it will be possible to make better and better estimations of how much blood must be collected in order to be able to foresee a successful fracture healing.

It is obvious to a skilled person that the instrument according to the present invention can be modified and altered within the scope of the subsequent claims without departing from the idea and purpose of the invention. Thus, the sleeve as well as the rod can e.g. be made of any suitable metal or plastic material and be given any other suitable configuration for the intended purpose. Preferably, when blood should be collected outside the sleeve, at least the inner side of the sleeve should comprise or be layered with a material having a very low friction, e.g. highly polished metal. The instrument may be configured for repeated use or may be configured for disposal after use.

The invention claimed is:

1. An instrument (1) for use in measuring blood flow in a femoral head (6), which measurement is to be performed after a femoral neck (5) fracture (7), wherein the instrument (1) comprises:
   a sleeve (2), configured for insertion into a bore (4) drilled in the femoral neck (5) and femoral head (6) and provided with at least one aperture (8) at a front portion (2a) thereof, said aperture (8) being intended for location in the femoral head (6) distally of the fracture (7) after insertion of the sleeve (2) into said bore (4), and
   a rod (3), displaceably mounted in the sleeve (2) and configured for closing said at least one aperture (8) in the sleeve (2) during insertion of the sleeve (2) into the bore (4) in the femoral neck (5) and femoral head (6) and for exposing said at least one aperture (8) after said insertion such that blood leaking into said bore (4) at said front portion (2a) of the sleeve (2) is collected by said sleeve (2) through said at least one aperture (8) therein, the rod (3) being configured to define, in the front portion (2a) of the sleeve (2), a reservoir (10) for the collected blood for subsequent measuring of a volume of the collected blood therein, wherein the reservoir (10) is a cavity inside at least the front portion (3a) of the rod (3), the reservoir (10) being defined by a front extremity of the rod (3), a bottom surface (14) of the rod (3) and a lateral surface (3aa) of the rod (3), the bottom surface (14) of the rod (3) being spaced apart from the front extremity of the rod (3), the lateral surface (3aa) of the rod (3) extending at least between the front extremity and bottom surface (14), the rod (3) further comprising at least one lateral aperture (13) in fluid communication with the reservoir (10).

2. The instrument (1) according to claim 1, wherein said at least one aperture (8) is provided in a lateral surface (2ab) of the front portion (2a) of the sleeve (2).

3. The instrument (1) according to claim 2, wherein the rod (3) comprises a front portion (3a) which is configured for closing said at least one aperture (8) in the lateral surface (2ab) in the front portion (2a) of the sleeve (2) by bringing said front portion (3a) into engagement with the aperture (8) in the lateral surface (2ab) of the sleeve (2) and which is rotatable, the at least one lateral aperture (13) arranged in the lateral surface (3aa) of the rod (3) for exposure of the aperture (8) in the sleeve (2) by rotation of the rod (3) such that the lateral aperture (13) in the front portion (3a) of the rod (3) is aligned with the aperture (8) in the sleeve (2).

* * * * *